United States Patent [19]

Lotsch

[11] Patent Number: 4,725,685
[45] Date of Patent: Feb. 16, 1988

[54] NOVEL ISOINDOLINE COMPOUNDS, THEIR METAL COMPLEXES AND THEIR USE AS PIGMENTS

[75] Inventor: Wolfgang Lotsch, Beindersheim, Fed. Rep. of Germany

[73] Assignee: BASF Aktiengesellschaft, Ludwigshafen, Fed. Rep. of Germany

[21] Appl. No.: 802,059

[22] Filed: Nov. 25, 1985

[30] Foreign Application Priority Data

Nov. 29, 1984 [DE] Fed. Rep. of Germany ....... 3443465

[51] Int. Cl.$^4$ .................. C07D 239/88; C07D 239/70
[52] U.S. Cl. ..................... 544/225; 544/249; 544/284
[58] Field of Search ........................................ 544/225

[56] References Cited

U.S. PATENT DOCUMENTS

| | | | |
|---|---|---|---|
| 4,002,635 | 1/1977 | Ofrey | 548/159 |
| 4,496,727 | 1/1985 | Jabal | 544/225 |
| 4,525,591 | 6/1985 | Lotsch et al. | 544/250 |

FOREIGN PATENT DOCUMENTS 3311375 10/1984 Fed. Rep. of Germany .

OTHER PUBLICATIONS

CRC Handbook of Chem. & Physics, (Weast, Ed), 1985-1986.
Condensed Chemical Dictionary, 10th Edition, p. 1036.
Cotton, Ed, "Advanced Inorganic Chemistry", p. 601.
Bailar, Ed, "Comprehensive Inorganic Chem.", vol. 4, (1973), p. 673.
CRC Handbook of Chemistry and Physics, Robert C. West, Ph.D., 1979-1980.

*Primary Examiner*—Mark L. Berch
*Attorney, Agent, or Firm*—Oblon, Fisher, Spivak, McClelland & Maier

[57] ABSTRACT

Isoindoline compounds of the formula (I)

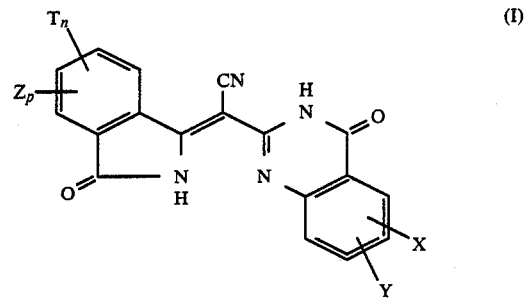

and their metal complexes of the formula (II)

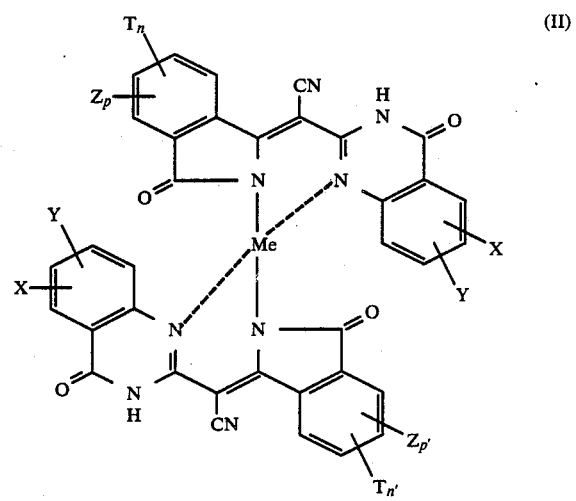

where (in formulae (I) and (II)) X and Y are each hydrogen, fluorine, chlorine, bromine, alkyl, alkoxy, alkoxycarbonyl, alkylsulfonyl, alkanoylamino, carbamyl, nitro, benzoylamino or N-phenylcarbamyl, or X and Y together form a radical of a fused benzene ring, T is fluorine, chlorine or bromine, Z is nitro, carbamyl, alkanoylamino, alkoxy, alkyl or phenyl, n and n' are each 0, 1, 2, 3 or 4, p and p' are each 0 or 1, the sums (n+p) and (n'+p') are each not more than 4, and Me is a divalent cation of a transition metal, of zinc or of cadmium, are useful pigments or coloring polymers, printing inks and finishes.

13 Claims, No Drawings

NOVEL ISOINDOLINE COMPOUNDS, THEIR METAL COMPLEXES AND THEIR USE AS PIGMENTS

The present invention relates to novel isoindoline compounds of the formula I

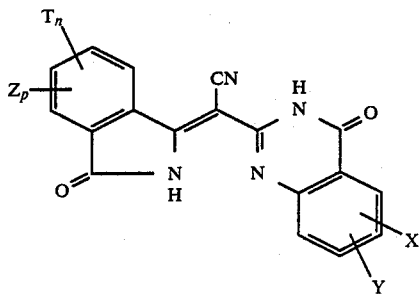

where X and Y independently of one another are each hydrogen, fluorine, chlorine, bromine, $C_1$–$C_4$-alkyl, $C_1$–$C_4$-alkoxy, $C_1$–$C_4$-alkoxycarbonyl, $C_1$–$C_4$-alkylsulfonyl, carbamyl, $C_1$–$C_4$-alkanoylamino or nitro or are each N-phenylcarbamyl or benzoylamino which is unsubstituted or substituted in the phenyl moiety, or X and Y together form a radical of a fused benzene ring, T is fluorine, chlorine or bromine, Z is nitro, carbamyl, $C_1$–$C_4$-alkanoylamino, $C_1$–$C_4$-alkoxy, $C_1$–$C_4$-alkyl or phenyl, n is 0, 1, 2, 3 or 4 and p is 0 or 1, and the sum (n+p) is not more than 4.

The present invention furthermore relates to novel metal complexes of isoindoline compounds of the formula (I), these complexes being of the formula (II)

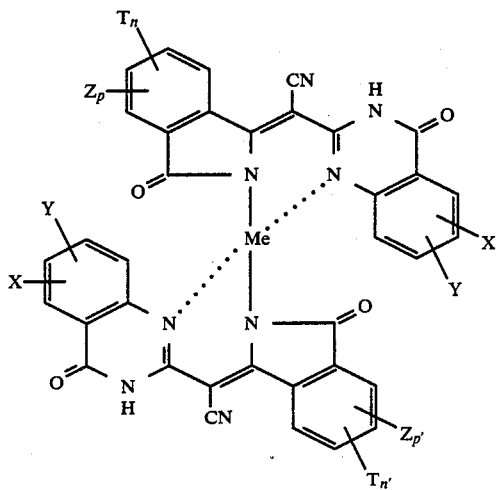

where X and Y independently of one another are each hydrogen, fluorine, chlorine, bromine, $C_1$–$C_4$-alkyl, $C_1$–$C_4$-alkoxy, $C_1$–$C_4$-alkoxycarbonyl, $C_1$–$C_4$-alkylsulfonyl, carbamyl, $C_1$–$C_4$-alkanoylamino or nitro or are each N-phenylcarbamyl or benzoylamino which is unsubstituted or substituted in the phenyl moiety, or X and Y together form a radical of a fused benzene ring, T is fluorine, chlorine or bromine, Z is nitro, carbamyl, $C_1$–$C_4$-alkanoylamino, $C_1$–$C_4$-alkoxy, $C_1$–$C_4$-alkyl or phenyl, n and n' are each 0, 1, 2, 3 or 4, p and p' are each 0 or 1, the sums (n+p) and (n'+p') are each not more than 4, and Me is a divalent cation of a transition metal, of zinc or of cadmium.

The novel compounds (I) and ((II) give greenish yellow to reddish yellow colorations.

The novel colorants are useful pigments which, in a finely divided form, can be used for pigmenting high molecular weight organic material, examples of suitable materials of this type being cellulose ethers and cellulose esters, such as ethylcellulose, nitrocellulose, cellulose acetate or cellulose butyrate; natural or synthetic resins, such as polymerization resins or condensation resins, eg. aminoplasts, in particular urea/formaldehyde resins, melamine/formaldehyde resins, alkyd resins, phenoplasts, polycarbonates or polyolefins, eg. polystyrene, polyvinyl chloride, polyethylene, polypropylene, polyacrylonitrile or polyacrylates; nylons, polyurethanes or polyesters; rubber, casein, silicone or silicone resins. These may be used alone or as mixtures.

Whether the stated high molecular weight compounds are in the form of plastic materials, melts or spinning solutions, finishes, surface coatings or printing inks is not critical. Depending on the intended use, it has proven advantageous to use the novel pigments as toners or in the form of preparations. In order to obtain finely divided pigments, it is often advantageous to subject them to a milling process.

The isoindoline compounds (I) are particularly useful for the mass coloring of thermoplastics, while the complexes (II) are useful not only for this purpose but also for pigmenting printing inks and finishes.

Compared with colorations produced with metal complexes of German Laid-Open Application DOS No. 2,359,791, the metal complexes of the invention give colorations which have a purer hue and greater depth.

Further specific examples of substituents X and Y in addition to those stated above are $C_1$–$C_4$-alkyl such as methyl, ethyl, n- and isopropyl, n- and isobutyl, 2-methylpropyl and tert.-butyl, $C_1$–$C_4$-alkoxy such as methoxy, ethoxy, n- and isopropoxy and n- and isobutoxy, $C_1$–$C_4$-alkylsulfonyl, such as methyl-, ethyl-, n-propyl- and n-butylsulfonyl, and alkanoylamino such as acetylamino, propionylamino and n- and isobutyrylamino.

X and Y independently of one another are each preferably hydrogen, chlorine or bromine or together form a radical of a fused benzene ring.

X and Y are each particularly preferably hydrogen.

T is preferably bromine or chlorine and n and n' are each preferably 0, 1 or 2.

Z is preferably nitro or $C_2$- or $C_3$-alkanoylamino and p and p' are each preferably 0 or 1.

p, p', n and n' are each, in particular, 0.

Specific examples of suitable transition metal ions Me for (II) are those of manganese, cobalt, cadmium, zinc, copper and nickel.

Me is preferably a divalent ion of cobalt, copper or nickel, in particular of cobalt.

Accordingly, preferred isoindoline compounds of the formula (I) are those in which X and Y independently of one another are each hydrogen, chlorine or bromine, or X and Y together form a radical of a fused benzene ring, and p is 0.

Particularly preferred compounds (I) are those in which X and Y are each hydrogen and n and p are each 0.

Preferred metal complexes of the formula (II) are those in which Me is a divalent cobalt, copper or nickel cation, particularly preferred metal complexes II being those in which Me is a cobalt ion.

Among these metal complexes, particularly preferred compounds are those in which X and Y independently of one another are each hydrogen, chlorine or bromine, or X and Y together form a radical of a fused benzene ring, and p and p' are each 0.

Very particularly preferred compounds (II) are those in which X and Y are each hydrogen, n, n', p and p' are each 0 and Me is a divalent cation of cobalt, of copper or of nickel. The cobalt complexes are particularly noteworthy.

The isoindoline compounds of the formula (I) are obtained in a conventional manner by condensation of a 2-cyanomethylquinazolone compound of the formula (III)

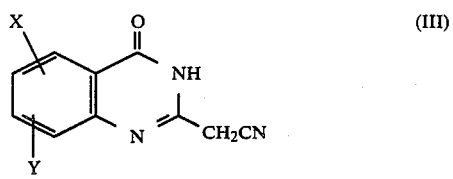

with an isoindolinone compound of the formula (IV)

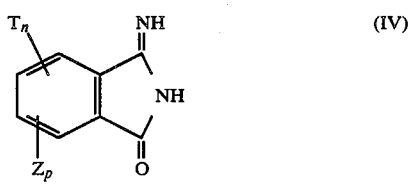

In the formulae (III) and (IV), X, Y, T, Z, p and n have the above meanings.

Advantageously, the condensation is carried out in an organic solvent, for example in an alcohol, such as methanol, ethanol, isopropanol, ethylene glycol monoethyl ether or diethylene glycol monoethyl ether, or in acetic acid, propionic acid or dimethylformamide, at elevated temperatures.

Since the condensates of the formula (I) are sparingly soluble in the stated agents, these condensates can be readily isolated by filtration. Any impurities present can be removed by washing.

To convert (I) to (II), the compounds (I) are treated with agents which donate divalent cations of the transition metals, of zinc or of cadmium, in particular those of nickel, of cobalt or of copper.

The formates, acetates or acetylacetonates of these metals, eg. nickel(II) acetate, copper(II) acetate or cobalt(II) acetate, are preferably used.

Metallization is advantageously effected in one of the above solvents or in a mixture of these, preferred solvents being dimethylformamide and diethylene glycol monoethyl ether.

By using mixtures of metal salts, mixtures of metal complexes of the formula (II) can be prepared.

It is also possible to carry out the condensation and the metallization in a single-vessel process.

The Examples which follow illustrate the preparation of the compounds (I) and (II). Parts and percentages are by weight.

EXAMPLE 1

19 parts of 2-cyanomethylquinazolone and 19 parts of iminophthalimide hydrochloride in 150 parts of glacial acetic acid were heated to 120° C., while stirring, and kept at this temperature for 5 hours. After the mixture had cooled, the precipitate was filtered off under suction, washed with methanol and water and dried at from 80° to 100° C. under reduced pressure to give 25 parts of the compound of the formula (I) where X and Y are each H and p and n are each 0.

When used for mass coloring of polystyrene, the compound gave pure greenish yellow lightfast colorations.

EXAMPLES 2 TO 15

The procedure described in Example 1 was followed, except that the cyanomethylquinazolones (III) and iminoisoindolinones (IV) stated in the Table below were used. The condensates of the formula (I) color polystyrene in the hues stated in column 4. The colorations possess fastness properties similar to those obtained with the colorant of Example 1.

| Example | (III) | (IV) | Color in polystyrene |
|---|---|---|---|
| 2 | 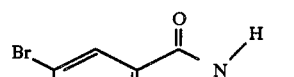 | 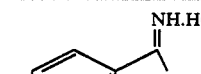 | greenish yellow |
| 3 |  |  | greenish yellow |

-continued

| Example | (III) | (IV) | Color in polystyrene |
|---|---|---|---|
| 4 | 3,4-dichloro-benzamide with N=C(CH2CN) | 3-imino-isoindolin-1-one·HCl | greenish yellow |
| 5 | 4-nitro-benzamide with N=C(CH2CN) | 3-imino-isoindolin-1-one·HCl | greenish yellow |
| 6 | 4-(CH3CONH)-benzamide with N=C(CH2CN) | 3-imino-isoindolin-1-one·HCl | neutral yellow |
| 7 | 4-(PhCONH)-benzamide with N=C(CH2CN) | 3-imino-isoindolin-1-one·HCl | neutral yellow |
| 8 | 5-bromo-3-chloro-benzamide with N=C(CH2CN) | 2 | greenish yellow |
| 9 | naphthalene-3-carboxamide with N=C(CH2CN) | 2 | neutral yellow |
| 10 | benzamide with N=C(CH2CN) | 5,6-dichloro-3-imino-isoindolin-1-one·HCl | yellow |
| 11 | benzamide with N=C(CH2CN) | 7-chloro-3-imino-isoindolin-1-one | yellow |
| 12 | benzamide with N=C(CH2CN) | 5,6-Br, 7-Cl-3-imino-isoindolin-1-one | yellow |

| Example | (III) | (IV) | Color in polystyrene |
|---|---|---|---|
| 13 | 2-(N-H amide)-phenyl-N=C-CH2CN | Cl-5,6- substituted isoindoline (NH, NH, =O) | yellow |
| 14 | 2-(N-H amide)-phenyl-N=C-CH2CN | O2N-5,6- substituted isoindoline (NH, NH, =O) | yellow |
| 15 | 2-(N-H amide)-phenyl-N=C-CH2CN | CH3CONH-5,6- substituted isoindoline (NH, NH, =O) | yellow |

EXAMPLE 16

26 parts of nickel acetate.4H₂O were added to 32 parts of the compound obtained as described in Example 1, in 300 parts of dimethylformamide, and the mixture was stirred for 16 hours at 150° C. The precipitate was filtered off under suction while hot and washed with methanol and water to give 26 parts of a greenish yellow pigment powder. When the pigment was incorporated into polyvinyl chloride on a roll mill, the yellow film obtained from the resulting material had good lightfastness and good fastness to migration. A finish pigmented with the resulting nickel complex showed very good lightfastness and fastness to weathering.

EXAMPLES 17 TO 19

The nickel acetate used in Example 16 was replaced with an equimolar amount of the metal salts stated in the Table. Pigments having the stated hues were obtained.

| Example | Metal salt | Color of the complex |
|---|---|---|
| 17 | cobalt acetate.4H₂O | reddish yellow |
| 18 | copper acetate.H₂O | yellow |
| 19 | zinc acetate.2H₂O | greenish yellow |

EXAMPLES 20 AND 21

Using a method similar to that described in Example 16, the isoindoline compounds (I) obtained as described in Examples 2 to 15 were reacted with the metal salts stated in the Table below; the corresponding complexes (II) were obtained, these complexes giving the hues stated in column 4.

| Example | (I) from Example | Metal salt | Hue |
|---|---|---|---|
| 20 | 2 | Ni(OAc)₂.4H₂O | greenish yellow |
| 21 | 2 | Co(OAc)₂.4H₂O | reddish yellow |
| 22 | 2 | Cu(OAc)₂.H₂O | yellow |
| 23 | 3 | Ni(OAc)₂.4H₂O | greenish yellow |
| 24 | 3 | Co(OAc)₂.4H₂O | reddish yellow |
| 25 | 3 | Cu(OAc)₂.H₂O | yellow |
| 26 | 4 | Ni(OAc)₂.4H₂O | greenish yellow |
| 27 | 4 | Co(OAc)₂.4H₂O | reddish yellow |
| 28 | 4 | Cu(OAc)₂.H₂O | yellow |
| 29 | 5 | Ni(OAc)₂.4H₂O | greenish yellow |
| 30 | 5 | Co(OAc)₂.4H₂O | reddish yellow |
| 31 | 5 | Cu(OAc)₂.H₂O | yellow |
| 32 | 6 | Ni(OAc)₂.4H₂O | greenish yellow |
| 33 | 6 | Co(OAc)₂.4H₂O | reddish yellow |
| 34 | 6 | Cu(OAc)₂.H₂O | yellow |
| 35 | 7 | Ni(OAc)₂.4H₂O | greenish yellow |
| 36 | 7 | Co(Oac)₂.4H₂O | reddish yellow |
| 37 | 7 | Cu(OAc)₂.H₂O | yellow |
| 38 | 8 | Ni(OAc)₂.4H₂O | greenish yellow |
| 39 | 8 | Co(OAc)₂.4H₂O | reddish yellow |
| 40 | 8 | Cu(OAc)₂.H₂O | yellow |
| 41 | 1 | Ni(OAc)₂.4H₂O | greenish yellow |
| 42 | 1 | Co(OAc)₂.4H₂O | reddish yellow |
| 43 | 1 | Cu(OAc)₂.H₂O | yellow |
| 44 | 10 | Ni(OAc)₂.4H₂O | greenish yellow |
| 45 | 10 | Co(OAc)₂.4H₂O | reddish yellow |
| 46 | 10 | Cu(OAc)₂.H₂O | yellow |
| 47 | 11 | Ni(OAc)₂.4H₂O | greenish yellow |
| 48 | 11 | Co(OAc)₂.4H₂O | reddish yellow |
| 49 | 11 | Cu(OAc)₂.H₂O | yellow |
| 50 | 12 | Ni(OAc)₂.4H₂O | greenish yellow |
| 51 | 12 | Co(OAc)₂.4H₂O | reddish yellow |
| 52 | 12 | Cu(OAc)₂.H₂O | yellow |
| 53 | 13 | Ni(OAc)₂.4H₂O | greenish yellow |
| 54 | 13 | Co(OAc)₂.4H₂O | reddish yellow |
| 55 | 13 | Cu(OAc)₂.H₂O | yellow |
| 56 | 14 | Ni(OAc)₂.4H₂O | greenish yellow |
| 57 | 14 | Co(OAc)₂.4H₂O | reddish yellow |
| 58 | 14 | Cu(OAc)₂.H₂O | yellow |
| 59 | 15 | Ni(OAc)₂.4H₂O | greenish yellow |
| 60 | 15 | Co(OAc)₂.4H₂O | reddish yellow |
| 61 | 15 | Cu(OAc)₂.H₂O | yellow |

OAc = acetate

EXAMPLES OF USE (a) Finish 10 parts of the colorant obtained as described in Example 16 and 95 parts of a baking finish mixture which contains 70% of coconut alkyd resin (60% strength solution in xylene) and 30% of melamine resin (about 55% strength solution in butanol/xylene) are milled in an attrition mill. After application and baking for 30 minutes at 120° C., greenish yellow full-shade coatings having good lightfastness and fastness to overspraying are obtained. Admixing titanium dioxide gives yellow colorations.

If the colorants described in Examples 17 to 61 are used, greenish to reddish yellow coatings having similar performance characteristics are obtained.

(b) Plastic 0.5 part of the colorant obtained as described in Example 1 is applied onto 100 parts of standard-grade polystyrene granules by tumbling, and the colored granules are homogenized by extrusion at from 190° to 195° C. Lightfast yellow extrudates are obtained.

If a mixture consisting of 0.5 part of colorant and 1 part of titanium dioxide is used, yellow colorations are likewise obtained.

If the pigments obtained as described in Examples 2 to 61 are used, yellow colorations having good lightfastness properties are obtained.

(c) Printing ink 8 parts of the pigment obtained as described in Example 1, 40 parts of a rosin modified with phenol formaldehyde, and from 55 to 65 parts of toluene are mixed thoroughly in a dispersing unit. The resulting toluene-based gravure printing ink gives greenish yellow lightfast prints.

I claim:

1. A metal complex of an isoindoline compound, which is of the formula (II)

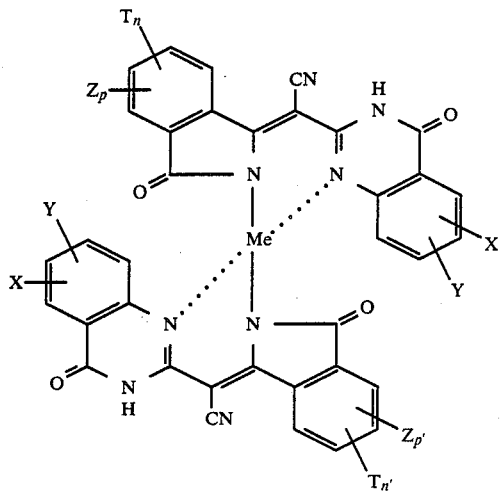

where X and Y independently of one another are each hydrogen, fluorine, chlorine, bromine, $C_1$-$C_4$-alkyl, $C_1$-$C_4$-alkoxy, $C_1$-$C_4$-alkoxycarbonyl, $C_1$-$C_4$-alkylsulfonyl, carbamyl, $C_1$-$C_4$-alkanoylamino, nitro, N-phenylcarbamyl or benzoylamino, or X and Y together with the carbons to which they are attached form a radical of a fused benzene ring, T is fluorine, chlorine or bromine, Z is nitro, carbamyl, $C_1$-$C_4$-alkanoylamino, $C_1$-$C_4$-alkoxy, $C_1$-$C_4$-alkyl or phenyl, n and n' are each 0, 1, 2, 3 or 4, p and p' are each 0 or 1, the sums (n+p) and (n'+p') are each not more than 4, and Me is a divalent cation of the transition metal series, of zinc, or of cadmium.

2. A metal complex as claimed in claim 1, wherein Me is a divalent cobalt, copper or nickel ion.

3. A metal complex as claimed in claim 1, wherein X and Y are each hydrogen, chlorine or bromine, or X and Y together form a radical of a fused benzene ring, and p and p' are each 0.

4. A metal complex as claimed in claim 2, wherein X and Y are each hydrogen, chlorine or bromine, or X and Y together form a radical of a fused benzene ring, and p and p' are each 0.

5. A metal complex as claimed in claim 1, wherein X and Y are each hydrogen and n, n', p and p' are each 0.

6. A metal complex as claimed in claim 2, wherein X and Y are each hydrogen and n, n', p and p' are each 0.

7. A metal complex as claimed in claim 1, wherein X and Y are each hydrogen, n, n', p and p' are each 0, and Me is a divalent cobalt ion.

8. The metal complex of claim 1, wherein X and Y are independently methyl, ethyl, n-propyl, iso-propyl, n-butyl, iso-butyl, 2-methylpropyl, tert-butyl, methoxy, n-propoxy, iso-propoxy, n-butoxy, iso-butoxy, methylsulfonyl, ethylsulfonyl, n-propylsulfonyl, n-butylsulfonyl, acetylamino, propionylamino, n-butyrylamino, or iso-butyrylamino.

9. The metal complex of claim 1, wherein T is bromine or chlorine, and n and n' are 0, 1 or 2.

10. The metal complex of claim 1, wherein Z is nitro or $C_2$-$C_3$-alkanoylamino, and p and p' are each 0 or 1.

11. The metal complex of claim 1, wherein p, p', n, and n' are each 0.

12. The metal complex of claim 1, wherein Me is manganese, cobalt, cadmium, zinc, copper or nickel.

13. The metal complex of claim 1, wherein Me is cobalt.

* * * * *